(12) United States Patent
Dexheimer

(10) Patent No.: US 7,135,427 B2
(45) Date of Patent: *Nov. 14, 2006

(54) CARBOXY-MODIFIED ALUMINUM-BASED CATALYST COMPOSITIONS

(75) Inventor: Edward Michael Dexheimer, Grosse Ile, MI (US)

(73) Assignee: BASF Corporation, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/151,077

(22) Filed: Jun. 13, 2005

(65) Prior Publication Data

US 2005/0234209 A1    Oct. 20, 2005

Related U.S. Application Data

(63) Continuation-in-part of application No. 10/036,679, filed on Dec. 21, 2001, now Pat. No. 6,919,486.

(51) Int. Cl.
*B01J 31/00* (2006.01)
*G07F 5/06* (2006.01)

(52) U.S. Cl. .............. 502/155; 502/170; 556/14; 556/179

(58) Field of Classification Search .............. 502/155, 502/170; 556/14, 179
See application file for complete search history.

(56) References Cited

U.S. PATENT DOCUMENTS

| | | | |
|---|---|---|---|
| 3,657,149 A | 4/1972 | Vandenberg et al. | |
| 3,657,159 A | 4/1972 | Vandenberg et al. | |
| 3,697,496 A | 10/1972 | Ueno et al. | |
| 4,209,609 A | 6/1980 | Haas | |
| 4,304,729 A | 12/1981 | Greco et al. | |
| 4,554,295 A | 11/1985 | Ridge, Jr. | |
| 4,721,817 A | 1/1988 | Edwards | |
| 4,810,729 A | 3/1989 | Davis et al. | |
| 5,053,148 A | 10/1991 | von Bonin | |
| 5,637,673 A | 6/1997 | Le-Khac | |
| 5,777,177 A | 7/1998 | Pazos | |
| 5,830,926 A | 11/1998 | Smiecinski et al. | |
| 5,919,988 A | 7/1999 | Pazos et al. | |
| 6,100,363 A | 8/2000 | Sampara et al. | |
| 6,103,850 A | 8/2000 | Reichel et al. | |
| 6,165,399 A | 12/2000 | Guntherberg et al. | |
| 6,197,839 B1 | 3/2001 | Genz et al. | |
| 6,228,899 B1 | 5/2001 | Wetterling et al. | |
| 6,284,812 B1 | 9/2001 | Rotermund et al. | |
| 6,310,114 B1 | 10/2001 | Genz et al. | |
| 6,319,985 B1 | 11/2001 | Bruning et al. | |
| 6,383,970 B1 | 5/2002 | Mimura et al. | |
| 6,492,565 B1 | 12/2002 | Denninger et al. | |
| 6,706,844 B1 | 3/2004 | Dexheimer | |
| 6,777,533 B1 | 8/2004 | Dexheimer | |
| 6,919,486 B1 | 7/2005 | Dexheimer | |

FOREIGN PATENT DOCUMENTS

| | | |
|---|---|---|
| DE | 1937728 | 2/1970 |
| DE | 10030413 | 3/2001 |
| EP | 273521 | 12/1987 |
| EP | 761708 | 8/1996 |
| EP | 992524 | 9/1999 |

OTHER PUBLICATIONS

PCT Search Report; PCT/EP02/10027.
Hong-Quan; Ring-Opening Polymerization of Epichlorohydrin and its Copolymerization With Other Alkylene Oxides by Quaternary Catalyst System; Department of Chemistry, Huazhong University of Science and Technology; May 20, 2000; P-2446-2454; Wuhan J. Applied Polymer Science, vol. 80, pp. 2446-2454 (2001).
Mark R. Mason; Alisa M. Perkins; Alkylaluminophosphonate-Catalyzed Ring-Opening Homopolymerization of Epichlorohydrin and Propylene Oxide; Journal of Organometallic Chemistry 599 (2000) 200-207; Toledo, Ohio.
PCT Search Report for PCT/EP02/06693.
Chemical Abstracts, vol. 76, No. 10, Mar. 6, 1972, Ueno et al.; "Polymerization Catalysts for Alkylene Oxides" XP002217502 Abstract & JP 07 130405A (Sumitomo Chemical Co. Ltd.).

*Primary Examiner*—J. A. Lorengo
*Assistant Examiner*—J. Pasterczyk
(74) *Attorney, Agent, or Firm*—Fernando A. Borrego

(57) ABSTRACT

A carboxy-modified aluminum-based catalyst composition is of the general formula $P(O)(OAlR'R'')_3$ or $RP(O)(OAlR'R'')_2$ wherein O represents oxygen, P represents pentavalent phosphorous, Al represents aluminum, R comprises hydrogen, an alkyl group, or an aryl group, and R' and R'' independently comprise a halide, an alkyl group, a haloalkyl group, an alkoxy group, an aryl group, an aryloxy group, or a carboxy group, so long as at least one of R' and R'' is a carboxy group. The carboxy-modified aluminum-based catalyst composition is, generally, the reaction product of phosphoric acid or a pentavalent phosphonic acid, a tri-substituted aluminum compound, and a carboxylic acid.

16 Claims, No Drawings

000# CARBOXY-MODIFIED ALUMINUM-BASED CATALYST COMPOSITIONS

RELATED APPLICATIONS

This application is a continuation-in-part of and claims the benefit of U.S. patent application Ser. No. 10/036,679, filed on Dec. 21, 2001, now U.S. Pat. No. 6,919,486, issued on Jul. 19, 2005.

TECHNICAL FIELD

The present invention generally relates to a catalyst composition. More specifically, the present invention relates to a carboxy-modified aluminum-based catalyst composition, such as a carboxy-modified aluminum phosphate or a carboxy-modified aluminum phosphonate, that is typically used to form a polyether polyol.

BACKGROUND OF THE INVENTION

Various catalyst compositions for use in forming polyoxyalkylene polyether polyols, i.e., polyether polyols, are known in the art. Polyether polyols, which are well known compounds, are utilized, in conjunction with a cross-linking agent, such as an organic isocyanate, to form or produce a variety of polyurethane products, foamed and non-foamed, i.e., elastomeric, such as polyurethane foams and polyurethane elastomers. As a general matter, these polyols are produced by polyoxyalkylation of an initiator molecule with an alkylene oxide such as ethylene oxide, propylene oxide, butylene oxides, or mixtures thereof. The initiator molecules contain alkylene oxide-reactive hydrogens like those found in hydroxyl groups and amine groups. This oxyalkylation is generally conducted in the presence of a catalyst composition.

The most common catalyst compositions are basic metal catalysts such as sodium hydroxide, potassium hydroxide, or alkali metal alkoxides. One advantage of these basic metal catalysts is that they are inexpensive and readily available. Use of these basic metal catalysts, however, is associated with a range of problems. One of the major problems is that oxyalkylation with propylene oxide has associated with it a competing rearrangement of the propylene oxide into allyl alcohol, which continually introduces a monohydroxyl-functional molecule. This monohydroxyl-functional molecule is also capable of being oxyalkylated. In addition, it can act as a chain terminator during the reaction with isocyanates to produce the final polyurethane product. Thus, as the oxyalkylation reaction is continued more of this unwanted product, generally measured as the unsaturation content of the polyol, is formed. This leads to reduced functionality and a broadening of the molecular weight distribution of the polyol. The amount of unsaturation content may approach 30 to 40 molar % with unsaturation levels of 0.090 meq KOH/g or higher.

In an attempt to reduce the unsaturation content of polyether polyols, a number of other catalyst compositions have been developed. One such group of catalysts includes the hydroxides formed from rubidium, cesium, barium, and strontium. These catalysts also present a number of problems. The catalysts only slightly reduce the degree of unsaturation, are much more expensive, and some are toxic.

A further line of catalyst development for polyether polyol production focuses on double metal cyanide (DMC) catalysts. These catalysts are typically based on zinc hexacyanocobaltate. With the use of DMC catalysts, it is possible to achieve relatively low unsaturation content in the range of 0.003 to 0.010 meq KOH/g. While the DMC catalysts would seem to be highly beneficial they also are associated with a number of difficulties. As a first difficulty, there is a relatively high capital cost involved in scaling up of and utilization of DMC catalysts. The catalysts themselves have an extremely high cost compared to the basic metal catalysts. Further, when forming a polyether polyol using a DMC catalyst, there is a significant initial lag time before the DMC catalyst begins to catalyze the reaction. It is not possible to add ethylene oxide onto growing polyol chains utilizing DMC catalysts. To add ethylene oxide to a growing chain, the DMC catalysts must be replaced with the typical basic metal catalysts, thus adding complexity and steps. In addition, it is generally believed that the DMC catalysts should be removed prior to work-up of any polyether polyol for use in forming polyurethane products. Finally, polyether polyols generated using DMC catalysts are not mere "drop in" replacements for similar size and functionality polyols produced using the typical basic metal catalysts. Indeed, it has been found that often DMC catalyzed polyether polyols have properties very different from equivalent polyether polyols produced using, for example, potassium hydroxide.

More recent lines of catalyst development for polyether polyol production focus on aluminum phosphate and aluminum phosphonate catalysts. However, these catalysts also have drawbacks. Both aluminum phosphate catalysts and aluminum phosphonate catalysts may be subject to slow hydrolysis upon exposure to water, such as the water present in the air as humidity or even water present as an impurity in the initiator molecule and alkylene oxide reactants.

Finally, it is known that simple carboxy-modified aluminum compounds, i.e., those not including phosphate and/or phosphonate, are not catalytically active and are, therefore, not useful for the formation of polyether polyols.

Thus, there exists a need for catalyst compositions that can be used for the oxyalkylation of initiator molecules by alkylene oxides that are inexpensive, capable of producing very low unsaturation polyether polyols, do not require removal from the polyether polyol prior to utilization to form a polyurethane product, and that produce a polyether polyol having properties that are the same or better than those in polyether polyols produced using basic metal catalysts. The need also extends to catalyst compositions that have improved stability as determined by resistance to hydrolysis upon exposure to water. It would also be beneficial if the new class of catalyst compositions could be used in existing systems and equipment using standard manufacturing conditions.

SUMMARY OF THE INVENTION AND ADVANTAGES

A carboxy-modified aluminum-based catalyst composition according to the present invention is of the general formula $P(O)(OAlR'R'')_3$ or $RP(O)(OAlR'R'')_2$. In this formula, O represents oxygen, P represents pentavalent phosphorous, Al represents aluminum, R comprises hydrogen, an alkyl group, or an aryl group, and R' and R'' independently comprise a halide, an alkyl group, a haloalkyl group, an alkoxy group, an aryl group, an aryloxy group, or a carboxy group, so long as at least one of R' and R'' is a carboxy group.

Importantly, the carboxy-modified aluminum based catalyst composition utilized in the present invention remains soluble in polyether polyols and has catalytic activity comparable to, if not exceeding that of, the basic metal and DMC catalysts. When the carboxy-modified aluminum-based catalyst composition is used in the oxyalkylation of initiator molecules by alkylene oxides, very low unsaturation (e.g. less than 0.080 meq KOH/g such as less than or equal to 0.020 meq KOH/g) polyether polyols are formed. Also, the catalyst composition used herein is inexpensive as compared to the DMC catalyst of the prior art. Furthermore, there is no need to remove, by neutralization and filtration, the catalyst composition or any of its residue from the polyether polyol prior to use of the polyether polyol in forming polyurethane products. Physical properties of polyether polyols that are produced with this catalyst composition are not negatively impacted, and the catalyst composition can be used in existing systems and equipment using standard manufacturing conditions.

The carboxy modification of this aluminum-based catalyst composition imparts stability on the catalyst composition. That is, this catalyst composition is stable in the sense that it is not moisture sensitive. As such, this catalyst composition does not hydrolyze upon exposure to water. Furthermore, the improved stability of the carboxy-modified aluminum-based catalyst composition of the present invention, as compared to the stability of the alkyl and alkoxy derivatives typically associated with more conventional aluminum-based catalysts, such as aluminum phosphate and aluminum phosphonate catalysts, provides for a greater freedom in manufacturing processes. For example, with the catalyst composition of the present invention, there is less concern for the amount of water present as humidity or as an impurity in the reactants. Finally, unlike the simple carboxy-modified aluminum compounds described above, the carboxy-modified aluminum-based catalyst compositions used in the present invention are catalytically active in the formation of polyether polyols.

DETAILED DESCRIPTION

A carboxy-modified aluminum-based catalyst composition is disclosed. The catalyst is used, as described in more detail below, in the formation of a polyether polyol. The polyether polyol, i.e., polyetherol, itself and a method of forming the polyether polyol are also disclosed herein. Generally, the method uses the catalyst composition to form the polyether polyol. It is to be understood that the terminology "carboxy" as used herein is interchangeable with the terminology "carboxylate". As such, the catalyst of the present invention is also appropriately referred to as a carboxylate-modified aluminum-based catalyst. For convenience in description, the carboxy-modified aluminum based catalyst composition is also referred to and described below simply as the catalyst composition or the catalyst.

Use of this catalyst enables production of polyether polyols having very low unsaturation as compared to a similarly sized polyether polyols produced using typical basic metal catalysts. In addition, other than the very low degree of unsaturation, polyether polyols formed via catalysis with the catalyst have properties that are the same or better than those produced using the typical basic metal catalysts. The catalyst can be synthesized in a very straightforward manner and is inexpensive compared to many of the other catalysts capable of producing these very low unsaturation polyether polyols. The carboxy-modified aluminum-based catalyst composition is stable in that it is not sensitive to moisture and therefore provides the advantage of freedom in manufacturing as described above. We have also found that the catalyst does not have to be removed after formation of the polyether polyol prior to its use in forming, i.e., producing, a polyurethane product. The polyurethane product can be foamed or non-foamed, i.e., elastomeric, and is described additionally below. The catalyst can be readily substituted in existing oxyalkylation procedures that utilize basic metal catalysts, such as potassium hydroxide, with virtually no modifications to the procedure. Unlike the DMC class of catalysts, the catalyst used in the present invention exhibit no lag time and are capable of polyoxyalkylation utilizing ethylene oxide.

The method of forming the polyether polyol includes the step of providing at least one alkylene oxide. Suitable alkylene oxides include, but are not limited to, ethylene oxide, propylene oxide, butylene oxide, epichlorohydrin or mixtures of these alkylene oxides. As is known, alkylene oxides are used to polyoxyalkylate an initiator molecule, described additionally below, to form polyether polyols.

The method of forming the polyether polyol also includes the step of providing at least one initiator molecule. As understood by those skilled in the art, the initiator molecule has at least one alkylene oxide reactive hydrogen. More preferred initiator molecules have at least two alkylene oxide reactive hydrogens. Suitable initiator molecules include, but are not limited to, an alcohol, a polyhydroxyl compound, a mixed hydroxyl and amine compound, an amine, a polyamine compound, or mixtures of these initiator molecules. Examples of alcohols include, but are not limited to, aliphatic and aromatic alcohols, such as lauryl alcohol, nonylphenol, octylphenol and $C_{12}$ to $C_{18}$ fatty alcohols. Examples of the polyhydroxyl compounds include, but are not limited to, diols, triols, and higher functional alcohols such as sucrose and sorbitol. Examples of amines include, but are not limited to, aniline, dibutylamine, and $C_{12}$ to $C_{18}$ fatty amines. Examples of polyamine compounds include, but are not limited to, diamines such as ethylene diamine, toluene diamine, and other polyamines.

In a preferred embodiment, a pre-reaction initiator molecule is pre-reacted with at least one alkylene oxide to form an oligomer. Typically, such an oligomer has a number average molecular weight of from 200 to 1,500 Daltons. The oligomer is then used as the initiator molecule and reacted with the alkylene oxide in the presence of the catalyst to form the polyether polyol as described below. Suitable pre-reaction initiator molecules include those described above in the context of the initiator molecule.

The at least one alkylene oxide is reacted with the at least one initiator molecule in the presence of the catalyst or residue thereof to form the polyether polyol. Without intending to be bound by theory, the catalyst may undergo exchange reactions to some extent with the initiator molecule(s) in a reversible manner to form a modified carboxy-modified aluminum-based compound, which is also catalytically active. This modified aluminum-based compound is also referred to as a residue. Preferably, the initiator molecule and the alkylene oxide or oxides are reacted in the presence of the catalyst for a period of time from 15 minutes to 15 hours. Typically, this period of time is sufficient to form polyether polyols having an equivalent weight of from 100 to 10,000, more preferably from 200 to 2,000, and most preferably from 500 to 2,000, Daltons. The reaction between the initiator molecule and the alkylene oxide is generally conducted at a temperature of from 95° C. to 150° C., and more preferably at a temperature of from 105° C. to 130° C.

Generally, the catalyst is utilized in an amount of from 0.1 to 5.0 weight percent based on the total weight of the polyether polyol, more preferably at levels of from 0.1 to 0.5 weight percent on the same basis. The catalyst composition of the present invention is of the general formula $P(O)(OAlR'R'')_3$ or $RP(O)(OAlR'R'')_2$.

When the catalyst composition is of the general formula P(O)(OAlR'R")$_3$, the catalyst composition is, more specifically, a carboxy-modified aluminum phosphate catalyst. In this formula, O represents oxygen, P represents pentavalent phosphorous, Al represents aluminum, R comprises hydrogen, an alkyl group, or an aryl group, and R' and R" independently comprise a halide, an alkyl group, a haloalkyl group, an alkoxy group, an aryl group, an aryloxy group, or a carboxy group, so long as at least one of R' and R" is a carboxy group. Examples of suitable haloalkyl groups include, but are not limited to, chloromethyl groups and trifluoromethyl groups. Where the carboxy-modified aluminum phosphate catalyst is used, it is possible for R' and R" to, more specifically, comprise one of an ethyl group, an ethoxy group, a propyl group, a propoxy group, a butyl group, a butoxy group, a phenyl group, or a phenoxy group, so long as one of R' and R" is the carboxy group. The carboxy group may also be referred to in the art as a carboxylate group. Further, as known to those skilled in the art, a carboxy, or carboxylate, group is a radical or moiety chemically represented as —COO$^-$. One preferred carboxy-modified aluminum phosphate catalyst comprises a tris[bis(carboxy)aluminum]phosphate catalyst. Examples of suitable tris[bis(carboxy)aluminum]phosphate catalysts include, but are not limited to, those selected from the group of tris(diacetoxyaluminum)phosphate, tris(dibenzoyloxyaluminum)phosphate, tris[bis(chloroacetoxy)aluminum]phosphate, tris[bis(dichloroacetoxy)aluminum]phosphate, tris[bis(trichloroacetoxy)aluminum]phosphate, tris[bis(trifluoroacetoxy)aluminum]phosphate, and mixtures thereof. As can be derived from the above examples, it is common for the carboxy group of the catalyst to comprise acetate, trifluoracetate, or dichloroacetate.

When the catalyst composition is of the general formula RP(O)(OAlR'R")$_2$, the catalyst composition is, more specifically, a carboxy-modified aluminum phosphonate catalyst. In this formula, just like that described above for the carboxy-modified aluminum phosphate catalyst, O represents oxygen, P represents pentavalent phosphorous, Al represents aluminum, R comprises hydrogen, an alkyl group, or an aryl group, and R' and W' independently comprise a halide, an alkyl group, a haloalkyl group, an alkoxy group, an aryl group, an aryloxy group, or a carboxy group, so long as at least one of R' and R" is a carboxy group. Examples of suitable haloalkyl groups include, but are not limited to, chloromethyl groups and trifluoromethyl groups. Where the carboxy-modified aluminum phosphonate catalyst is used, it is possible for R' and R" to, more specifically, comprise one of an ethyl group, an ethoxy group, a propyl group, a propoxy group, a butyl group, a butoxy group, a phenyl group, or a phenoxy group, so long as one of R' and R" is the carboxy group. One preferred carboxy-modified aluminum phosphonate catalyst comprises a bis[bis(carboxy)aluminum]phosphonate catalyst. Examples of suitable bis[bis(carboxy)aluminum]phosphonate catalysts include, but are not limited to, those selected from the group of bis(diacetoxyaluminum)methylphosphonate, bis(dibenzoyloxyaluminum)methylphosphonate, bis[bis(chloroacetoxy)aluminum]methylphosphonate, bis[bis(dichloroacetoxy)aluminum]methylphosphonate, bis[bis(trichloroacetoxy)aluminum]methylphosphonate, bis[bis(trifluoroacetoxy)aluminum]methylphosphonate, bis(diacetoxyaluminum)phenylphosphonate, bis(dibenzoyloxyaluminum)phenylphosphonate, bis[bis(chloroacetoxy)aluminum]phenylphosphonate, bis[bis(dichloroacetoxy)aluminum]phenylphosphonate, bis[bis(trichloroacetoxy)aluminum]phenylphosphonate, bis[bis(trifluoroacetoxy)aluminum]phenylphosphonate, and mixtures thereof. As can be derived from the above examples, it is common for the carboxy group of the catalyst to comprise acetate, trifluoracetate, or dichloroacetate.

The catalyst composition of the present invention which, preferably, comprises the reaction product of phosphoric acid or a pentavalent phosphonic acid, a tri-substituted aluminum compound, and a carboxylic acid, can be produced by a number of processes. The production of the catalyst is described in greater detail below in the Examples. When producing a carboxy-modified aluminum phosphate catalyst, the procedure generally involves reacting phosphoric acid and a tri-substituted aluminum compound to produce an aluminum phosphate catalyst. As is known, the phosphoric acid has the structure of PO(OH)$_3$, wherein: P represents a pentavalent phosphorous; O represents oxygen; and H represents hydrogen. The tri-substituted aluminum compounds are of the general formula of AlR'''$_3$, wherein: R''' comprises a halide, an alkyl group, a haloalkyl group, an alkoxy group, an aryl group, or an aryloxy group. Al represents aluminum. Some examples of tri-substituted aluminum compounds include, but are not limited to, trimethylaluminum, triethylaluminum, triethoxyaluminum, tri-n-propylaluminum, tri-n-propoxyaluminum, tri-iso-propoxyaluminum, tri-iso-butylaluminum, tri-sec-butylaluminum, tri-iso-butoxyaluminum, tri-sec-butoxyaluminum, tri-tert-butoxyaluminum, triphenylaluminum, tri-phenoxyaluminum, and mixtures thereof. Once the aluminum phosphate catalyst is produced, a solution of a carboxylic acid, such as acetic acid, dichloroacetic acid, trifluoracetic acid, or even mixtures of these three carboxylic acids, is introduced and added to the aluminum phosphate catalyst to produce the carboxy-modified aluminum phosphate catalyst.

When producing a carboxy-modified aluminum phosphonate catalyst, the procedure generally involves reacting a pentavalent phosphonic acid with a tri-substituted aluminum compound to produce an aluminum phosphonate catalyst. The pentavalent phosphonic acids that are suitable have the general structure of RPO(OH)$_2$, wherein: R comprises hydrogen, an alkyl group, or an aryl group; P represents a pentavalent phosphorous; O represents oxygen; and H represents hydrogen. Some examples include phosphonic acid, methylphosphonic acid, ethylphosphonic acid, propylphosphonic acid, iso-, tert-, or sec-butylphosphonic acids, phenylphosphonic acid, and mixtures thereof. The tri-substituted aluminum compounds are the same as those described above in the context of the carboxy-modified aluminum phosphate catalyst. Once the aluminum phosphonate catalyst is produced, a solution of a carboxylic acid, such as acetic acid, dichloroacetic acid, trifluoracetic acid, or even mixtures of these three carboxylic acids, is introduced and added to the aluminum phosphonate catalyst to produce the carboxy-modified aluminum phosphonate catalyst.

The polyether polyols formed via the reaction of the at least one alkylene oxide with the at least one initiator molecule in the presence of the catalyst according to the present invention have very low unsaturation. More specifically, the polyether polyols formed according to the present invention typically have an unsaturation of less than or equal to 0.020 meq KOH/g, more preferably less than or equal to 0.015 meq KOH/g, and most preferably less than or equal to 0.010 meq KOH/g. Furthermore, as described above, the polyether polyols formed according to the present invention typically have an equivalent weight of from 100 to 10,000, more preferably from 200 to 2,000, and most preferably from 500 to 2,000, Daltons. The polyether polyols formed according to the method of the present invention include, after formation of the polyether polyol, the catalyst or residue thereof. That is, the polyether polyol can comprise the catalyst or residue thereof. If so, the catalyst is preferably present in an amount of from 0.1 to 5.0 weight percent based on the total weight of the polyether polyol. The catalyst or its residue can even remain in the polyether polyol as the polyether polyol is used to make polyurethane products. There is no need to remove, by neutralization and/or filtration, the catalyst or any of its residues from the polyether polyol prior to use of the polyether polyol to form polyurethane products. Remaining amounts of the catalyst in the polyether polyol and, ultimately, in the final polyurethane product do not negatively impact the desired properties in the final polyurethane product. Optionally, it is to be understood that the remaining amounts of the catalyst can be removed by methods known and understood by those skilled in the art as desired.

As described immediately below, the polyether polyol is used in conjunction with a cross-linking agent, such as an organic isocyanate (including an organic polyisocyanates) and/or an isocyanate pre-polymer, to produce the polyurethane product. The polyether polyol has reactive hydrogens. It is to be understood that the polyether polyol can be included in a polyol component having at least one of the polyether polyols and, preferably, including a blend of more than one polyether polyol. Preferably, the polyether polyol has an equivalent weight of from about 100 to about 10,000.

The polyurethane product is formed by reacting at least one organic isocyanate and/or isocyanate pre-polymer with the polyether polyol. More specifically, the organic isocyanate and/or isocyanate pre-polymer have functional groups that are reactive to the reactive hydrogens of the polyether polyol. Suitable organic isocyanates include, but are not limited to, diphenylmethane diisocyanate (MDI), toluene diisocyanate (TDI), polymeric diphenylmethane diisocyanate (PMDI), and mixtures thereof.

In addition to the polyether polyol, other additional substances having reactive hydrogens may also participate in the reaction. Examples of such additional substances include, but are not limited to, amines and chain extenders, such as diols and triols. The polyether polyol and the organic isocyanate and/or isocyanate pre-polymer may, optionally, be reacted in the presence of a urethane promoting catalyst and certain additives including, but not limited to, blowing agents (if the polyurethane product is foamed), cross-linkers, surfactants, flame retardants, fillers, pigments, antioxidants, and stabilizers. The urethane promoting catalyst is different than the carboxy-modified aluminum-based catalyst of the present invention. The polyurethane products formed according to the methods of the present invention include flexible foams, semi-rigid foams, rigid foams, coatings, and elastomers such as adhesives, sealants, thermoplastics, and combination thereof.

As alluded to above, the catalyst or its residue can remain in the polyether polyol as the polyether polyol is used to make polyurethane products. In other words, there is no need to remove, by neutralization and/or filtration, the catalyst or any of its residues from the polyether polyol prior to use of the polyether polyol to form polyurethane products. As such, in one embodiment of the present invention, the polyurethane product comprises greater than 0.001, more preferably from 0.001 to 5.0, weight percent of the catalyst and/or catalyst residues based on the total weight of the polyurethane product.

The present invention also includes a particular composition of matter. The composition of matter includes a polyurethane material and the catalyst having $P(O)(OAlR'R'')_3$ or $RP(O)(OAlR'R'')_2$ as its general structure as described above, or residues of the catalyst. The polyurethane material can be the final polyurethane product. In any event, the polyurethane material is the reaction product of the polyether polyol and an organic isocyanate (including organic polyisocyanates) and/or isocyanate pre-polymer. Also, the polyurethane material can be foamed or non-foamed, i.e., elastomeric, and is, therefore, preferably selected from the group of flexible foams, semi-rigid foams, rigid foams, and elastomers such as coatings, adhesives, sealants, thermoplastics, and combinations thereof. In this embodiment of the composition of matter, the catalyst is preferably present in an amount of from approximately 0.001 to 5.0 weight percent based on the total weight of the polyurethane material, and the catalyst has the general structure of $P(O)(OAlR'R'')_3$ or $RP(O)(OAlR'R'')_2$ wherein O, P, Al, R, R', and R'' are as described above, again so long as at least one of R' and R'' are a carboxy group. It is possible for R' and R'' to, more specifically, comprise one of an ethyl group, an ethoxy group, a propyl group, a propoxy group, a butyl group, a butoxy group, a phenyl group, or a phenoxy group, so long as one of R' and R'' are the carboxy group.

EXAMPLES

The following Examples illustrate the nature of the subject method invention with regard to the synthesis of the carboxy-modified aluminum-based catalyst composition (e.g. carboxy-modified aluminum phosphate catalysts and carboxy-modified aluminum phosphonate catalysts) and with regard to the formation of polyether polyols in the presence of the carboxy-modified aluminum-based catalyst. These Examples also illustrate the production of the polyurethane product and/or composition of matter of the present invention using the carboxy-modified aluminum-based catalyst compositions and polyether polyols of the Examples. The Examples presented herein are intended to illustrate, and not to limit, the subject invention.

Example 1

Synthesis of Tris(di-sec-butoxyaluminum)Phosphate

To produce, for example, Tris(di-sec-butoxyaluminum) phosphate as an aluminum phosphate catalyst, the procedure more specifically includes placing a solution of 147.6 g (0.6 mole) of aluminum tri-sec-butoxide in 600 ml of dry THF in a 3 L round bottom flask equipped with mechanical stirring and a nitrogen atmosphere. The solution is cooled to 0° C. in a dry ice/isopropanol mixture. A solution of 17.0 g (0.2 mole) of polyphosphoric acid in 400 ml of isopropyl alcohol cooled to 0° C. is prepared by stirring magnetically in a nitrogen atmosphere. The solution is rapidly added to the flask thereby creating a clear, pink solution. After stirring 0.5 hr., the solution is allowed to warm to room temperature and stand overnight. The reaction mixture is then concentrated under vacuum, diluted with 500 mL of toluene, and further concentrated to a slightly viscous clear solution weighing 307.3 g, which represents ~30% of the aluminum phosphate catalyst in toluene.

Example 2

Synthesis of Tris[bis(trifluoroacetoxy)aluminum]Phosphate

To produce, for example, tris[bis(trifluoroacetoxy)aluminum]phosphate as the carboxy-modified aluminum phosphate catalyst composition, the procedure more specifically includes taking 161.6 g (0.10 mole) of a 39% solids solution of the aluminum phosphate catalyst synthesized in Example 1 and dissolving this solution in 200 ml of THF in a 1 L round bottom flask equipped with mechanical stirring and a nitrogen atmosphere. The solution is cooled to −68° C. in a dry ice/isopropanol mixture. A solution of 57.0 g (0.5 mole) of trifluoroacetic acid in 100 ml of THF is added dropwise over 1.5 hr. A clear solution is produced and this clear solution is allowed to slowly warm to room temperature. The clear solution is then concentrated by distillation off of the THF under vacuum, is stirred over calcium carbonate to remove any free acid, and is filtered to yield a clear, reddish-yellow solution. Further concentration of a portion of the clear, reddish-yellow solution yields a highly crystalline solid.

Example 3

Synthesis of Bis[bis(dichloroacetoxy)aluminum]Phenylphosphonate

To produce, for example, bis[bis(dichloroacetoxy)aluminum]phenylphosphonate as the carboxy-modified aluminum phosphonate catalyst composition, the procedure more specifically includes dissolving 100.4 g of aluminum phosphonate catalyst, specifically bis(di-sec-butyoxyaluminum)phenylphosphonate in this Example, in 300 ml of THF in a 1 L round bottom flask equipped with mechanical stirring and a nitrogen atmosphere. The solution is cooled to −10° C. in a dry ice/isopropanol mixture. A solution of 45.2 g of dichloroacetic acid in 200 ml of THF is added dropwise over approximately 1.5 hr. A clear solution is produced and this clear solution is allowed to slowly warm to room temperature. The clear solution is then concentrated by distillation off of the THF under vacuum.

Example 4

Synthesis of Bis[bis(trifluoroacetoxy)aluminum] Phenylphosphonate

To produce, for example, bis[bis(trifluoroacetoxy)aluminum]phenylphosphonate as the carboxy-modified aluminum phosphonate catalyst composition, the procedure more specifically includes dissolving 93.0 g of aluminum phosphonate catalyst, specifically bis(di-sec-butyoxyaluminum)phenylphosphonate in this example, in 600 ml of THF in a 2 L round bottom flask equipped with mechanical stirring and a nitrogen atmosphere. The solution is cooled to −72° C. in a dry ice/isopropanol mixture. A solution of 39.9 g of trifluoroacetic acid in 400 ml of THF is added dropwise over approximately 1.5 hr. A clear solution is produced and this clear solution is allowed to slowly warm to room temperature. The clear solution is then concentrated by distillation off of the THF under vacuum and heat.

Example 5

Formation of a Polyether Polyol 669.2 g of PLURACOL® Polyol GP 730, a 700 mol. wt. glycerin propoxylate, is charged to a 1-gallon autoclave that has already been flushed with nitrogen. The autoclave is sealed, heated to 110° C., and stripped of volatiles for approximately 0.5 hour at <10 mm Hg. The vacuum is relieved with nitrogen. The autoclave is cooled to 80° C. 110 g of the carboxy-modified aluminum phosphonate catalyst solution of Example 3 is then charged. The autoclave is the sealed, heated to 120° C., and stripped of volatiles for approximately 0.5 hour at <10 mm Hg. The vacuum is relieved with nitrogen. Propylene oxide is added as fast as possible at <90 psig and 120° C. until 2052.4 g are added and is reacted to a constant pressure at 120° C. for a maximum of 5 hrs. Heating and stirring are continued for this 5 hrs. after the addition is complete. The autoclave is evacuated to <10 mm Hg for 1 hour and is vented to 0–2 psig with nitrogen. The polyether polyol weighs 2771 g, representing a 97.9% yield. Analysis by gel permeation chromatography shows the peak molecular weight to be 1847 Daltons which corresponds to an equivalent weight of 615 Daltons. The degree of unsaturation is below the detection limit of the analytical method.

Example 6

Formation of a Polyether Polyol 730 g of PLURACOL® Polyol GP 730, a 700 mol. wt. glycerin propoxylate, is charged to a 1-gallon autoclave that has already been flushed with nitrogen. The autoclave is sealed, heated to 110° C., and stripped of volatiles for approximately 0.5 hour at <10 mm Hg. The vacuum is relieved with nitrogen. The autoclave is cooled to 80° C. 80 g of the carboxy-modified aluminum phosphonate catalyst solution of Example 4 is then charged. The autoclave is the sealed, heated to 120° C., and stripped of volatiles for approximately 0.5 hour at <10 mm Hg. The vacuum is relieved with nitrogen. Propylene oxide is added as fast as possible at <90 psig and 130° C. until 2239 g are added and is reacted to a constant pressure at 130° C. for a maximum of 5 hrs. Heating and stirring are continued for this 5 hrs. after the addition is complete. The autoclave is evacuated to <10 mm Hg for 1 hour and is vented to 0–2 psig with nitrogen. The polyether polyol weighs 2973 g, representing a 97.5% yield. Analysis by gel permeation chromatography shows the peak molecular weight to be 2008 Daltons which corresponds to an equivalent weight of 670 Daltons. The degree of unsaturation is below the detection limit of the analytical method.

Example 7

Formation of a Polyether Polyol 730 g of PLURACOL® Polyol GP 730, a 700 mol. wt. glycerin propoxylate, and 80 g of the carboxy-modified aluminum phosphate catalyst solution of Example 2, are charged to a 1-gallon autoclave that has already been flushed with nitrogen. The autoclave is sealed, heated to 110° C., and stripped of volatiles for approximately 0.5 hour at <10 mm Hg. The vacuum is relieved with nitrogen. Propylene oxide is added as fast as possible at <90 psig and 130° C. until 2239 g are added and is reacted to a constant pressure at 130° C. for a maximum of 5 hrs. Heating and stirring are continued for this 5 hrs. after the addition is complete. The autoclave is evacuated to <10 mm Hg for 1 hour and is vented to 0–2 psig with nitrogen. The polyether polyol weighs 2489 g, representing an 81.1% yield. Analysis by gel permeation chromatography shows the peak molecular weight to be 1540 Daltons which corresponds to an equivalent weight of 515 Daltons. The degree of unsaturation is below the detection limit of the analytical method.

Example 8

Formation of a Polyether Polyol/Oxypropylenation of a Diol Initiator Molecule

A 1 gallon nitrogen flushed autoclave is charged with 400 g of a polypropylene glycol having a number average molecular weight of 700 and 100 g of a 25% by weight solution of tris[bis(trifluoroacetoxy)aluminum]phosphate in toluene and tetrahydrofuran, with agitation. The solvent is removed by batch vacuum stripping at 110° C. for 0.5 hours. Then 1886 g of propylene oxide is fed into the autoclave at a rate of approximately 300 g/hour, at 110° C. and a pressure of less than 90 psig. The contents are reacted to constant pressure at 110° C. for approximately 5 hours. The autoclave is then evacuated to less than 10 mm Hg for 60 minutes. The vacuum is then relieved. The resultant polyetherol is a clear fluid having a number average molecular weight of about 5000, a hydroxyl number of about 22 meq KOH/g, and an unsaturation of less than about 0.010 meq KOH/g.

Example 9

Formation of a Polyether Polyol/Oxypropylenation of a Triol Initiator Molecule

A 5 gallon nitrogen flushed autoclave is charged with 1900 g of a glycerin propylene oxide adduct oligomer having a number average molecular weight of 700 and 220 g of a 25% by weight solution of bis[bis(dichloroacetoxy)aluminum]phenylphosphonate in toluene and tetrahydrofuran, with agitation. The solvent is removed by batch vacuum stripping at 110° C. for 0.5 hours. Then 14100 g of propylene oxide is fed into the autoclave at a rate of approximately 1000 g/hour, at 110° C. and a pressure of less than 90 psig. The rate of propylene oxide addition is adjusted as needed to maintain the concentration of unreacted propylene oxide at or below 8%. The contents are reacted to constant pressure at 110° C. for approximately 5 hours. The autoclave is then evacuated to less than 10 mm Hg for 60 minutes. The vacuum is then relieved with nitrogen, the contents cooled to 105° C. and transferred to a standard filter mix tank for removal of the catalyst. The contents are treated with 500 g of Magnesol® and 120 g of water for 1 hour at 105° C. The treated contents are recycled through the filter element until the filtrate is haze free indicating full removal of the particulate Magnesol® with bound catalyst. These filtration procedures are well known in the art and can comprise use of systems as simple as Buchner funnels with medium weight filter paper designed to remove particles in the size range of greater than 50 to 100 microns. The filtrate was then heated to 105° C. and vacuum stripped at less than 10 mm Hg for 1 hour. After 1 hour the vacuum is relieved with nitrogen. The clear fluid polyetherol has a number average molecular weight of about 6000, a hydroxyl number of about 28 meq KOH/g, and an unsaturation of less than about 0.010 meq KOH/g.

Example 10

Formation of a Polyether Polyol/Oxyalkylenation of a Triol Initiator Molecule

A 5 gallon nitrogen flushed autoclave is charged with 3528 g of a glycerin propylene oxide adduct oligomer having a number average molecular weight of 700 and 250 g of a 25% by weight solution of bis[bis(trifluoroacetoxy)aluminum]phenylphosphonate in toluene and tetrahydrofuran, with agitation. The solvent is removed by batch vacuum stripping at 110° C. for 0.5 hours. Then a mixture of 8304 g of propylene oxide and 2010 g of ethylene oxide is fed into the autoclave at a rate of approximately 1000 g/hour, at 110° C. and a pressure of less than 90 psig. The contents are reacted to constant pressure at 110° C. for approximately 3 hours. The autoclave is then vented to 34 psig and 1780 g of propylene oxide is fed at a rate of 2000 g/hour into the autoclave at 110° C. and a pressure of less than 90 psig. The contents are reacted to constant pressure at 110° C. for no more than 5 hours. The autoclave is then evacuated to less than 10 mm Hg for 60 minutes. Then the vacuum is relieved with nitrogen and the polyol recovered. The clear fluid polyetherol has a number average molecular weight of about 2000–2500, a hydroxyl number of about 75 meq KOH/g, and an unsaturation of less than about 0.020 meq KOH/g.

Example 11

Formation of a Polyether Polyol/Oxyalkylenation of a Triol Initiator Molecule

A 1 gallon nitrogen flushed autoclave is charged with 700 g of a glycerin propylene oxide adduct oligomer having a number average molecular weight of 700 and 100 g of a 25% by weight solution of tris[bis(trifluoroacetoxy)aluminum]phosphate in toluene and tetrahydrofuran, with agitation. The solvent is removed by batch vacuum stripping at 110° C. for 0.5 hours. Then 2020 g of propylene oxide is fed into the autoclave at a rate of approximately 1000 g/hour, at 110° C. and a pressure of less than 90 psig. The contents are reacted to constant pressure at 110° C. for approximately 3 hours. The autoclave is then vented to 34 psig and 415 g of ethylene oxide is fed at a rate of 400 g/hour at 110° C. and a pressure of less than 90 psig. The contents are reacted to constant pressure at 110° C. for approximately 3 hours. The autoclave is then evacuated to less than 10 mm Hg for 60 minutes. Then the vacuum is relieved with nitrogen and the polyol recovered. The clear fluid polyetherol has a number average molecular weight of about 3000–3500, a hydroxyl number of about 50–56 meq KOH/g, and an unsaturation of about 0.010 meq KOH/g.

Example 12

Formation of a Polyether Polyol/Terminal Capping with Ethylene Oxide of a Triol Oligomer A 1 gallon nitrogen flushed autoclave is charged with 2000 g of a glycerin propylene oxide adduct oligomer having a number average molecular weight of 3200 and 25 g of an approximately 40% by weight solution of bis[bis(dichloroacetoxy)aluminum]phenylphosphonate in toluene and tetrahydrofuran, with agitation. The solvent is removed by batch vacuum stripping at 125° C. for 0.5 hours. Then 360 g of ethylene oxide is fed into the autoclave at a rate of approximately 600 g/hour, at 130° C. and a pressure of less than 90 psig. The contents are reacted to constant pressure at 130° C. for approximately 1 hour. The autoclave is then evacuated to less than 10 mm Hg for 60 minutes. Then the contents are cooled to 80° C., the vacuum is relieved with nitrogen and the polyol is recovered. The clear fluid polyetherol has a number average molecular weight of about 5000 and a hydroxyl number of about 35 meq KOH/g, indicating addition of approximately 38 ethylene oxides per oligomer.

Example 13A (Comparative Example)

Synthesis of Di-sec-butoxyaluminum Trifluoroacetate

A simple carboxy-modified aluminum compound, i.e., one not including phosphate and/or phosphonate, was synthesized to confirm its catalytic activity or lack of catalytic activity in forming a polyether polyol (see Example 13B). The simple carboxy-modified aluminum compound in this Example is di-sec-butoxyaluminum trifluoroacetate. To form the di-sec-butoxyaluminum trifluoroacetate, 49.2 g of aluminum tri-sec-butoxide is dissolved in 600 mL of THF in a 2 L round bottom flask using a magnetic stirring bar. The solution is chilled to −72° C. in a dry ice bath. A solution of 22.42 g of trifluoroacetic acid in 400 mL of THF is added dropwise over a 2 hr period to the first solution. Reaction is allowed to continue for 40 min. at −72° C. The dry ice bath was removed and the reaction mixture was allowed to warm slowly to room temperature. The clear solution was then concentrated to 198 g by distillation off of the THF under vacuum and heat.

Example 13B (Comparative Example)

Attempted Formation of a Polyether Polyol 40 g of PLURACOL® Polyol GP 410, a 400 mol. wt. polypropylene glycol, and 6.0 g of the carboxy-modified aluminum compound of Example 13A are charged to a 500 mL round bottom flask equipped with a dry ice condenser. The flask is heated to 105° C. and stripped of volatiles for approximately 1 hour at 25 mm Hg. The vacuum is relieved with nitrogen. 5 g of propylene oxide is added, causing a heavy reflux. Heating and stirring are continued for 2 hrs. without the propylene oxide being consumed and the experiment associated with Example 13B is aborted.

Example 14

Comparison of KOH Catalyzed Polyols with Carboxy-modified Aluminum-based Catalyst Catalyzed Polyols Three different sized polyether polyols (Examples 14A–14C) are prepared using a triol initiator molecule and KOH catalyst. More specifically, Example 14A is alkoxylated with propylene oxide. Examples 14B and 14C are alkoxylated with propylene oxide and then capped with ethylene oxide. The physical properties associated with these comparative polyether polyols are presented in Table 1 below.

TABLE 1

| Example (Catalyst Used) | Number average molecular weight | Hydroxyl number meq KOH/g | Unsaturation meq KOH/g | Theoretical Functionality | Actual Functionality (due to unsaturation) |
|---|---|---|---|---|---|
| 14A (KOH) | 3,366 | 50.0 | 0.028 | 3.00 | 2.81 |
| 14B (KOH) | 4,808 | 35.0 | 0.050 | 3.00 | 2.57 |
| 14C (KOH) | 6,327 | 26.6 | 0.090 | 3.00 | 2.17 |

The above examples demonstrate the extraordinary value of the catalyst of the present invention. The polyether polyols produced using the carboxy-modified aluminum-based catalysts have a much higher functionality, as compared to polyether polyols produced using the KOH catalyst, due to the much lower unsaturation level for similarly sized polyols. Those skilled in the art recognize that actual functionality can be calculated from the theoretical functionality, the hydroxyl number, and the amount of the unsaturation formed.

The carboxy-modified aluminum-based catalyst compositions can be used in the present invention to provide terminal capping of polyols with an alkylene oxide. The suitable alkylene oxides include ethylene oxide, propylene oxide, butylene oxide and epichlorohydrin, among others. When capping with the ethylene oxide, the amount of terminal cap preferably ranges from 5 to 80% by weight based on the total weight of the polyetherol, and more preferably 5 to 20% by weight. When capping with propylene oxide, the amount of terminal cap preferably ranges from 5 to 80% by weight based on the total weight of the polyetherol, and more preferably 5 to 15% by weight.

Example 15

Formation of Foamed Polyurethane Products

Following the general procedure outlined above in Example 9, a triol polyether polyol is formed using a carboxy-modified aluminum-based catalyst composition, such as tris[bis(trifluoroacetoxy)aluminum]phosphate, and an initiator mixture of glycerin and a small amount of dipropylene glycol. The resultant triol polyether polyol is designated below as "Polyol A". The aluminum phosphate catalyst is not removed from Polyol A. In this particular example, the polyether polyol, Polyol A, has a number average molecular weight of about 2500, a hydroxyl number of about 60 meq KOH/g, and an unsaturation of less than about 0.015 meq KOH/g.

Following the general procedure outlined above in Example 9, a similarly sized triol polyether polyol is formed using KOH catalyst and the same initiator mixture (glycerin and a small amount of dipropylene glycol). The resultant triol polyether polyol is designated below as "Polyol B". The KOH catalyst is removed from Polyol B. In this particular examples, the polyether polyol, Polyol B, has a number average molecular weight of about 2600, a hydroxyl number of about 58 meq KOH/g, and an unsaturation of about 0.030 meq KOH/g.

Each polyol is then used to form a foamed polyurethane product (hereinafter simply referred to as foam or foams). The foams are prepared using conventional procedures known in the art and the components listed in Table 2 below. The amount of tin catalyst is slightly increased in Foam A because of the acidity of the residual phosphate.

TABLE 2

| Component | Foam A (amount in grams) | Foam B (amount in grams) |
| --- | --- | --- |
| Polyol A | 400.00 | 0.00 |
| Polyol B | 0.00 | 400.00 |
| Dabco ® 33-LV amine | 0.25 | 0.25 |
| BF-2370 surfactant | 1.00 | 1.00 |
| Water | 4.00 | 4.00 |
| T-10 tin catalyst | 0.60 | 0.45 |
| Toluene diisocyanate | 212.20 | 210.30 |

Foam A has the advantage of being produced with Polyol A which, as described above, has much lower unsaturation as compared to Polyol B. Furthermore, there is no need to remove the carboxy-modified aluminum based catalyst composition from Polyol A prior to preparation of Foam A.

The invention has been described in an illustrative manner, and it is to be understood that the terminology which has been used is intended to be in the nature of words of description rather than of limitation. Obviously, many modifications and variations of the present invention are possible in view of the above teachings. It is, therefore, to be understood that within the scope of the claims the invention may be practiced otherwise than as specifically described.

What is claimed is:

1. A carboxy-modified aluminum-based catalyst composition of the general formula P(O)(OAlR'R")$_3$ or RP(O)(OAlR'R")$_2$ wherein;
   R comprises hydrogen, an alkyl group, or an aryl group, and
   R' and R" independently comprise a halide, an alkyl group, a haloalkyl group, an alkoxy group, an aryl group, an aryloxy group, or a carboxy group,
   so long as at least one of R' and R" is a carboxy group.

2. A catalyst composition as set forth in claim 1 wherein said carboxy group comprises acetate, trifluoroacetate, or dichloroacetate.

3. A catalyst composition as set forth in claim 1 wherein said catalyst composition is a carboxy-modified aluminum phosphate catalyst of the general formula P(O)(OAlR'R")$_3$.

4. A catalyst composition as set forth in claim 3 wherein said carboxy-modified aluminum phosphate catalyst comprises a tris[bis(carboxy)aluminum]phosphate catalyst.

5. A catalyst composition as set forth in claim 4 wherein said tris[bis(carboxy)aluminum]phosphate catalyst is selected from the group of tris(diacetoxyaluminum)phosphate, tris(dibenzoyloxyaluminum)phosphate, tris[bis(chloroacetoxy)aluminum]phosphate, tris[bis(dichloroacetoxy)aluminum]phosphate, tris[bis(trichloroacetoxy)aluminum]phosphate, tris[bis(trifluoroacetoxy)aluminum]phosphate, and mixtures thereof.

6. A catalyst composition as set forth in claim 1 wherein said catalyst composition is a carboxy-modified aluminum phosphonate catalyst of the general formula RP(O)(OAlR'R")$_2$.

7. A catalyst composition as set forth in claim 6 wherein said carboxy-modified aluminum phosphonate catalyst comprises a bis[bis(carboxy)aluminum]phosphonate catalyst.

8. A catalyst composition as set forth in claim 7 wherein said bis[bis(carboxy)aluminum]phosphonate catalyst is selected from the group of bis(diacetoxyaluminum)methylphosphonate, bis(dibenzoyloxyaluminum)methylphosphonate, bis[bis(chloroacetoxy)aluminum]methylphosphonate, bis[bis(dichloroacetoxy)aluminum]methylphosphonate, bis[bis(trichloroacetoxy)aluminum]methylphosphonate, bis[bis(trifluoroacetoxy)aluminum]methylphosphonate, bis(diacetoxyaluminum)phenylphosphonate, bis(dibenzoyloxyaluminum)phenylphosphonate, bis[bis(chloroacetoxy)aluminum]phenylphosphonate, bis[bis(dichloroacetoxy)aluminum]phenylphosphonate, bis[bis(trichloroacetoxy)aluminum]phenylphosphonate, bis[bis(trifluoroacetoxy)aluminum]phenylphosphonate, and mixtures thereof.

9. A carboxy-modified aluminum-based catalyst composition comprising the reaction product of:
   phosphoric acid or a pentavalent phosphonic acid;
   a tri-substituted aluminum compound; and
   a carboxylic acid.

10. A catalyst composition as set forth in claim 9 wherein said pentavalent phosphonic acid is of the general formula RPO(OH)$_2$ wherein;
    R comprises hydrogen, an alkyl group, or an aryl group.

11. A catalyst composition as set forth in claim 10 wherein said pentavalent phosphonic acid is selected from the group of phosphonic acid, methylphosphonic acid, ethylphosphonic acid, propylphosphonic acid, iso-butylphosphonic acid, tert-butylphosphonic acid, sec-butylphosphonic acid, phenylphosphonic acid, and mixtures thereof.

12. A catalyst composition as set forth in claim 9 wherein said catalyst composition is a carboxy-modified aluminum phosphonate catalyst.

13. A catalyst composition as set forth in claim 9 wherein said catalyst composition is a carboxy-modified aluminum phosphate catalyst.

14. A catalyst composition as set forth in claim 9 wherein said carboxylic acid is selected from the group of acetic acid, dichloroacetic acid, trifluoroacetate acid, and mixtures thereof.

15. A catalyst composition as set forth in claim 9 wherein said tri-substituted aluminum compound is of the general formula AlR'''$_3$ wherein;
    R''' comprises a halide, an alkyl group, a haloalkyl group, an alkoxy group, an aryl group, or an aryloxy group.

16. A catalyst composition as set forth in claim 15 wherein said tri-substituted aluminum compound is selected from the group of trimethylaluminum, triethylaluminum, triethoxyaluminum, tri-n-propylaluminum, tri-n-propoxyaluminum, tri-iso-propoxyaluminum, tri-iso-butylaluminum, tri-sec-butylaluminum, tri-iso-butoxyaluminum, tri-sec-butoxyaluminum, tri-tert-butoxyaluminum, triphenylaluminum, triphenoxyaluminum, and mixtures thereof.

* * * * *